United States Patent
Parsonnet et al.

(10) Patent No.: US 7,826,895 B2
(45) Date of Patent: *Nov. 2, 2010

(54) ORGAN REJECTION MONITORING

(75) Inventors: Victor Parsonnet, Millburn, NJ (US); William J. Combs, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/460,724

(22) Filed: Jul. 28, 2006

(65) Prior Publication Data

US 2007/0010759 A1    Jan. 11, 2007

Related U.S. Application Data

(63) Continuation of application No. 10/299,397, filed on Nov. 20, 2002, now Pat. No. 7,130,679.

(51) Int. Cl.
*A61B 5/05* (2006.01)

(52) U.S. Cl. ...................................................... 600/547

(58) Field of Classification Search ................. 600/547, 600/508, 549; 607/1–3, 40, 50, 61, 63, 116; 128/897–899
See application file for complete search history.

(56) References Cited

U.S. PATENT DOCUMENTS

| | | | | |
|---|---|---|---|---|
| 5,246,008 A | * | 9/1993 | Mueller | 600/508 |
| 6,198,965 B1 | * | 3/2001 | Penner et al. | 600/547 |
| 6,970,741 B1 | * | 11/2005 | Whitehurst et al. | 607/3 |
| 7,130,679 B2 | * | 10/2006 | Parsonnet et al. | 600/547 |
| 2003/0199783 A1 | * | 10/2003 | Bloom et al. | 600/549 |
| 2003/0216663 A1 | * | 11/2003 | Jersey-Willuhn et al. | 600/547 |
| 2004/0092841 A1 | * | 5/2004 | Singer | 600/547 |

* cited by examiner

*Primary Examiner*—Max Hindenburg
*Assistant Examiner*—Brian Szmal
(74) *Attorney, Agent, or Firm*—Michael C. Soldner

(57) ABSTRACT

The invention is directed to techniques for monitoring organ rejection. An implanted device monitors the impedance of the transplanted organ. When the impedance measurements indicate that the organ is being rejected, the device provides early warning of rejection.

35 Claims, 6 Drawing Sheets

ORGAN REJECTION MONITORING

RELATED APPLICATION

This application is a continuation of U.S. patent application Ser. No. 10/299,397, entitled "ORGAN REJECTION MONITORING," filed Nov. 20, 2002 now U.S. Pat. No. 7,130,679 and is incorporated herein by reference in its entirety.

TECHNICAL FIELD

The invention relates to organ transplants, and more particularly, to monitoring a patient having a transplanted organ.

BACKGROUND

Transplantation of organs has become a widely practiced medical procedure. Organs such as a heart, lungs, kidney, pancreas and liver may be harvested from a donor and transplanted in a recipient. Although the risk of organ rejection has been reduced by the discovery of immunosuppressant drugs such as cyclosporine, organ rejection remains a major complication for patients undergoing organ transplantation.

A body receiving a donated organ naturally treats the organ as foreign tissue. The immune system of the recipient, which protects the body from infection, attacks the transplanted organ and tries to destroy it. Immunosuppressant drugs suppress the immune system so that the new organ will not be attacked and damaged. Organ recipients take immunosuppressive drugs for the rest of their lives to ward off rejection.

Even with immunosuppressive therapy, however, the immune system may try to reject the organ. Consequently, transplant recipients should be monitored for signs of rejection. Rejection typically manifests itself as inflammation in the organ, accompanied by edema. Conventional monitoring of organ rejection may be invasive or non-invasive. Conventional non-invasive techniques generally monitor rejection indirectly, such as by monitoring changes in blood chemistry. A conventional invasive technique is a tissue biopsy, in which a physician inserts a biopsy needle through the skin into the organ, and takes a sample of the transplanted organ for inspection under a microscope. Following transplant surgeries, biopsies may be performed frequently, but biopsies are usually performed less frequently following recovery.

SUMMARY

In general, the invention is directed to non-invasive techniques for monitoring organ rejection directly. An implanted device monitors organ rejection and provides early warning of rejection. The monitoring may be provided on a substantially continuous basis. In the event organ rejection is detected, early medical intervention will reduce organ damage, reduce hospitalizations and improve patient outcomes.

The implanted device includes at least two electrodes coupled to the organ. The device delivers a known excitation current to the organ via a set of electrodes, and monitors the response to the excitation current with the same or a different set of electrodes. In particular, the device monitors the differential voltage that develops in response to the excitation current. With the known current and the measured voltage, the impedance of the organ may be determined.

The impedance of the organ is related to the degree of rejection of the organ. In particular, an organ under attack from the immune system experiences inflammation, accompanied by edema. The edema, or fluid buildup, causes the impedance of the organ to be different when the organ is inflamed than when the organ is not inflamed. As a result, rejection of the organ may be monitored directly by monitoring the impedance of the organ.

There may be many techniques for monitoring organ rejection by monitoring impedance. The impedance of the transplanted organ may be monitored with respect to a baseline impedance value, or the impedance of the transplanted organ may be monitored with respect to a reference impedance value from a reference organ, or the impedance of the transplanted organ may be monitored for a change in variations of periodic impedance values. A monitoring device may employ any combination of these techniques.

In one embodiment, the invention is directed to an implantable medical device comprising an impedance measuring circuit and a processor. The impedance measuring circuit makes measurements of the impedance across at least a portion of a transplanted organ in a patient, and the processor determines whether the patient is experiencing rejection of the transplanted organ as a function of the impedance measurements. The device may also include a communication module that generates a signal when the processor determines that the patient is experiencing rejection of the transplanted organ. The signal alerts the patient or another person to seek prompt medical attention.

In another embodiment, the invention is directed to a method comprising sensing an impedance across at least a portion of a transplanted organ in a patient and determining whether the patient is experiencing rejection of the transplanted organ as a function of the impedance. The method may include any of the techniques mentioned above for determining whether the patient is experiencing rejection. The invention also includes a computer-readable medium comprising instructions for causing a programmable processor to carry out the method.

The invention may offer many advantages. For example, the invention provides for monitoring for signs of rejection on a substantially continuous basis, far more frequently than monitoring by biopsy. In addition, the invention may provide for supplying notice promptly when organ rejection is indicated. With the invention, the patient has an enhanced chance of early detection of organ rejection. Early detection may lead to prompt medical intervention, which in turn will reduce organ damage, reduce hospitalizations and improve patient outcomes.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
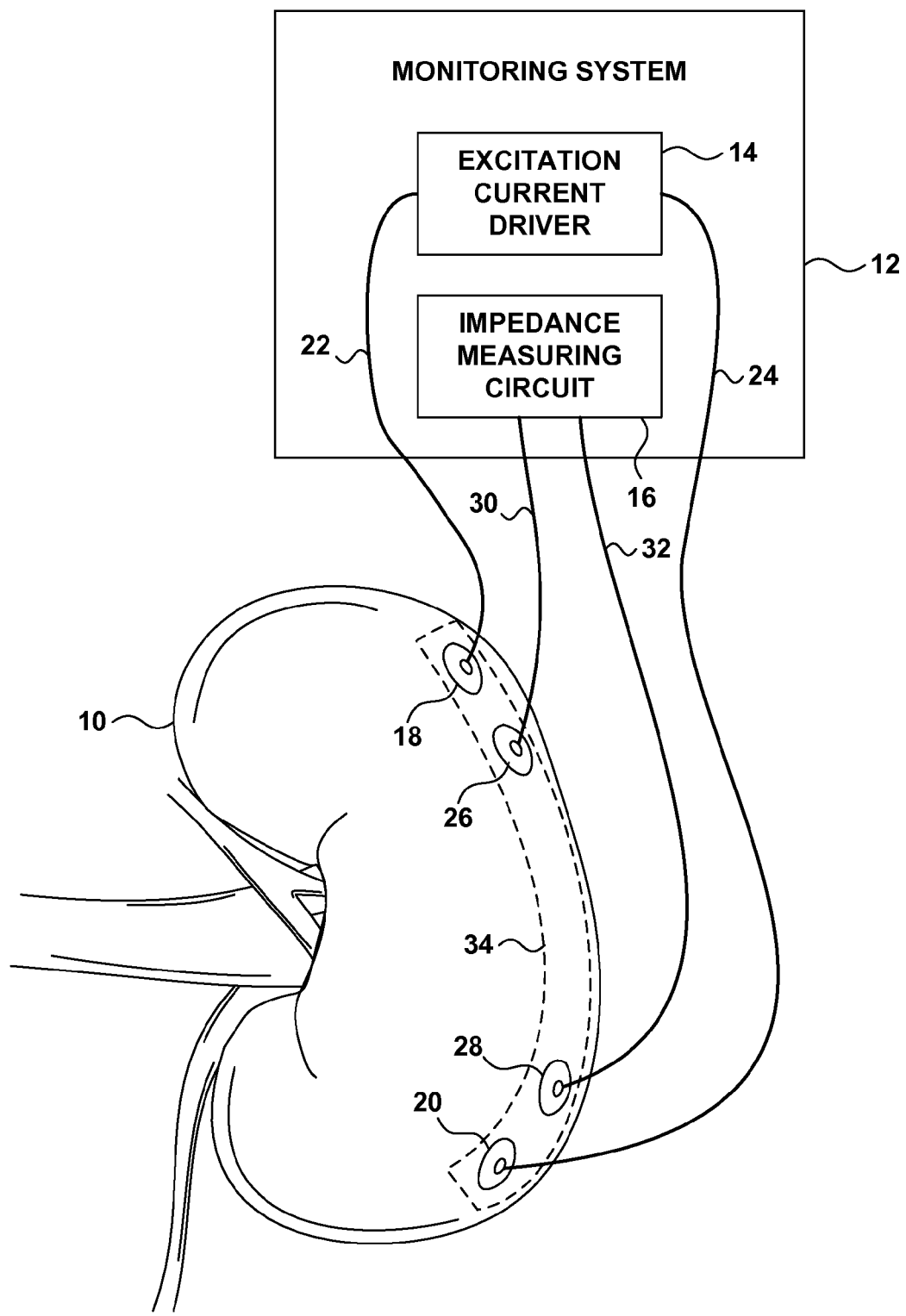
FIG. 1 is a schematic drawing of a kidney with electrodes to monitor impedance.

FIG. 1 depicts a kidney 10 in the body of a patient. Kidney 10 is a transplanted organ, and is at risk of being rejected by the body of the patient. A monitoring system 12, implanted in the body of the patient, monitors kidney 10 for signs of rejection. Monitoring system 12 provides monitoring on a substantially continuous basis, permitting early detection of organ rejection, thereby increasing the opportunity for early medical intervention.

Monitoring system 12 monitors kidney 10 by monitoring the impedance characteristics of kidney 10. In general, rejection typically manifests itself as inflammation, accompanied by edema. Edema is a swelling of the tissues as a result of excess interstitial fluid. Because of inflammation and edema, the impedance characteristics of a rejected kidney differ from the impedance characteristics of a kidney that does not experience rejection. By monitoring the impedance of kidney 10, monitoring system 12 thereby monitors kidney 10 for signs of inflammation and edema, which may indicate rejection.

Monitoring system 12 includes an excitation current driver 14 and an impedance measuring circuit 16. Excitation current driver 14 supplies a known excitation current to kidney 10. Impedance measuring circuit 16 measures the impedance by measuring the voltage that develops as a result of the application of the excitation current. The impedance is a function of the excitation current and the measured voltage.

FIG. 1 shows a quadripolar system with four electrodes. Electrodes 18 and 20 on the surface of kidney 10 are coupled to excitation current driver 14 via leads 22 and 24. Similarly, electrodes 26 and 28 on the surface of kidney 10 are coupled to impedance measuring circuit 16 via leads 30 and 32. Electrodes 18, 20, 26 and 28 may be arranged substantially linearly in a row 34 on the surface of kidney 10. Electrodes 18 and 20 form an outer pair of electrodes of row 34, and electrodes 26 and 28 form an inner pair.

The electrodes need not located on the surface of the organ as shown in FIG. 1. In some implementations of the system, one or more electrodes may be implanted or embedded in the organ. Electrodes 18, 20, 26 and 28 may therefore be located in the cortex of kidney 10.

Excitation current driver 14 drives an excitation current between electrodes 18 and 20 substantially along row 34. Impedance measuring circuit 16 measures the voltage that develops between electrodes 26 and 28 in response to application of the excitation current. Impedance measuring circuit 16 may have a high input impedance and consequently electrodes 26 and 28 cause negligible current division of the excitation current.

The quadripolar system shown in FIG. 1 is for purposes of illustration. More or fewer electrodes may be employed. In one alternate embodiment of the invention, for example, a single pair of electrodes may be used to deliver excitation current and measure the developed voltage. In another embodiment, excitation current driver 14 and impedance measuring circuit 16 may share a common electrode. The common electrode may be included in the housing for the implanted monitoring system. In addition, the arrangement of the electrodes in a single row as shown in FIG. 1 is an exemplary arrangement. Electrodes may be arranged in any of several configurations.

Figure 2:
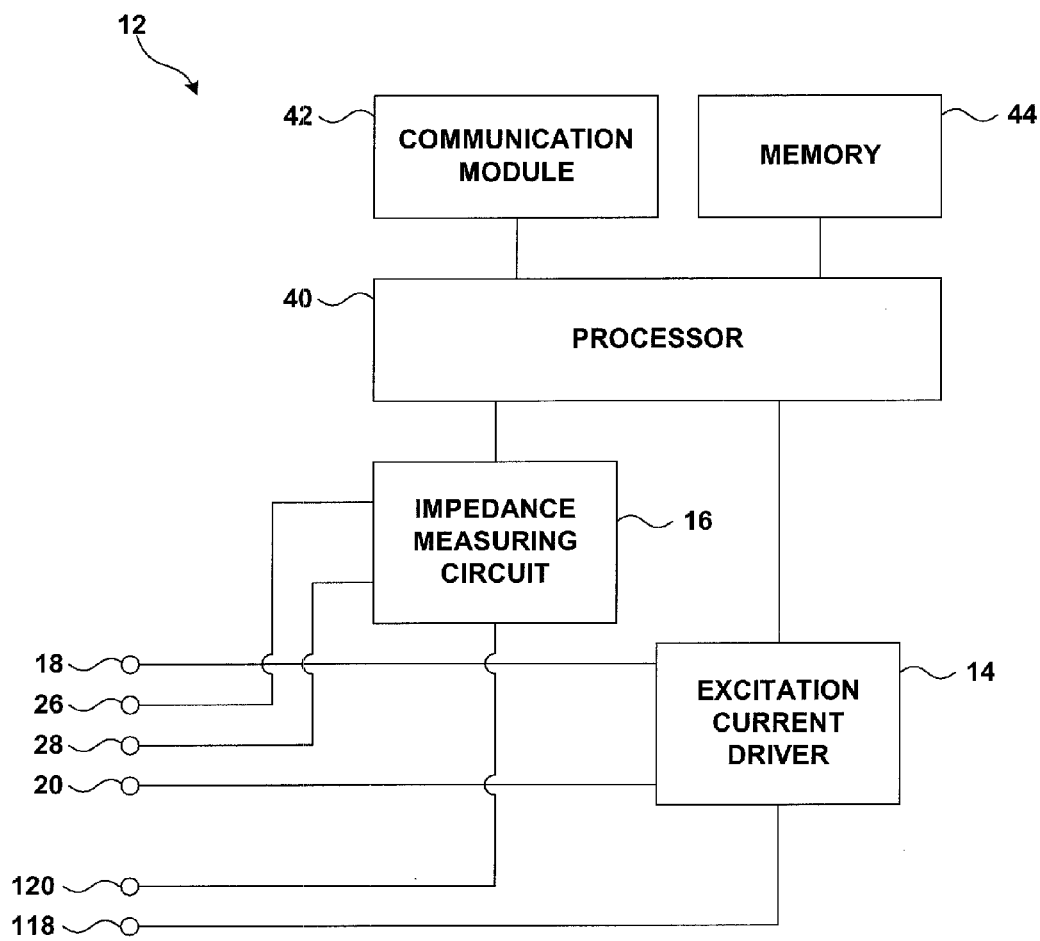
FIG. 2 is a block diagram illustrating a system for monitoring the impedance of a transplanted organ.

FIG. 2 is a block diagram showing an exemplary monitoring system 12. Monitoring system 12 may be implanted in a human body. As shown in FIG. 2, excitation current driver 14 and impedance measuring circuit 16 are controlled by a processor 40. Processor 40 regulates the timing of impedance measurements and interprets the significance of the obtained impedance measurements. Processor 40 further determines whether the impedance measurements indicate organ rejection or otherwise warrant generation of an alert or other communication via communication module 42. Processor 40 may take the form of a microprocessor, digital signal processor (DSP), application-specific integrated circuit (ASIC), field-programmable gate array (FPGA), or other logic circuitry programmed or otherwise configured to operate as described herein.

Communication module 42 may be any input/output device or combination of input/output devices. In one implementation, for example, communication module 42 may comprise a transducer that emits an audible signal when an alert is warranted, thereby notifying the patient or another person of a potentially serious condition. In another implementation, communication module 42 may comprise a wireless telemetry unit that communicates with another communication unit (not shown in FIG. 2) outside the body of the patient. The communication unit may in turn relay the alert to the patient, to the physician for the patient, or to another person. The alert may relayed to a remote person via any communication network, such as a telephone network or the Internet.

A memory unit 44 stores impedance measurements. Processor 40 evaluates the impedance measurements stored in memory 44 over time, and compares impedance measurements to a standard, such as a baseline impedance or an impedance of a reference organ. Monitoring system 12 may include additional electrodes, such as, e.g., electrodes 118, 120 for supplying an excitation current to and measuring the impedance of a reference organ. The reference organ may be a natural, i.e., non-transplanted, organ. As will be described below, impedance measurements from a reference organ may be used in place of or as a supplement to baseline impedance measurements.

As will be described below, a change in impedance measurements over time may indicate a possible organ rejection. When processor 40 detects a possible organ rejection, processor 40 may generate an alert or other notification via communication module 42. When processor 40 issues an alert via communication module 42, patient may be alerted to see a physician promptly. Communication module 42 may also identify the circumstances that gave rise to the alert. By alerting the patient to see a physician, organ rejection may be detected at virtually any time, and need not be detected during an office or hospital visit. An alert may also lead to early medical intervention, which will reduce organ damage, reduce hospitalizations and improve patient outcomes.

Monitoring system 12 may further include a power supply (not shown in FIG. 2). A typical power supply includes a battery. The power supply, along with the other components shown in FIG. 2, may be implanted in the body of a patient.

Figure 3:
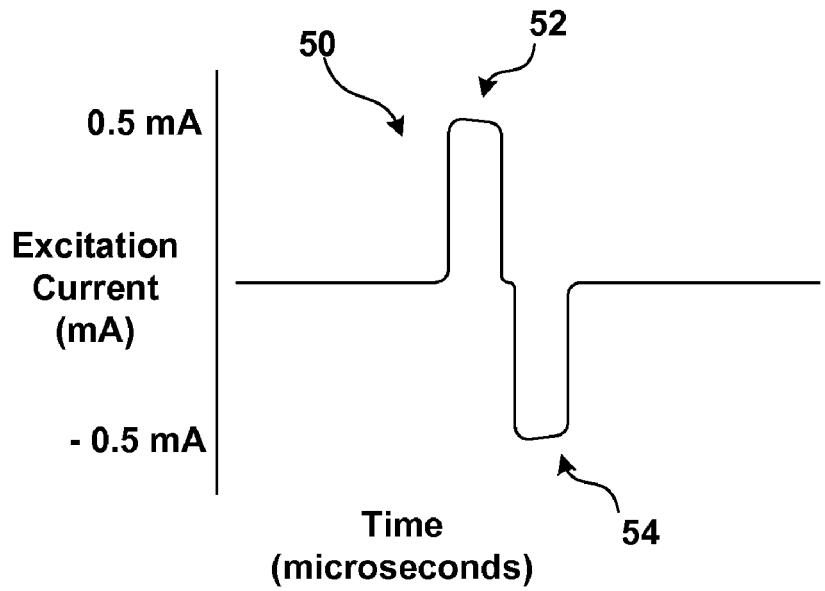
FIG. 3 shows a waveform of an exemplary excitation current applied by the system of FIG. 2.

FIG. 3 shows exemplary excitation current 50, comprising two current pulses 52 and 54 of opposite polarity, i.e., biphasic current pulses. Each current pulse 52, 54 may have an amplitude of approximately 0.5 milliamperes, and a pulse width of about 15 microseconds. The fundamental frequency of excitation 50 may be approximately 30 kHz, a frequency that is often used for measuring impedance of body tissues.

The excitation current for measuring impedance may be of any magnitude, frequency or shape. The waveform of excitation current 50 is advantageous, however, because delivery of pulses 52 and 54 consumes relatively little energy in comparison to, for example, a 30 kHz sinusoid. As a result, delivery of pulses 52, 54 extends the useful life of the implanted power supply. Excitation waveform 50 may be delivered, for example, once every minute or once during any other time interval. In this way, power may be conserved and measurement of the impedance of the transplanted organ may be monitored on a very frequent basis.

Figure 4:
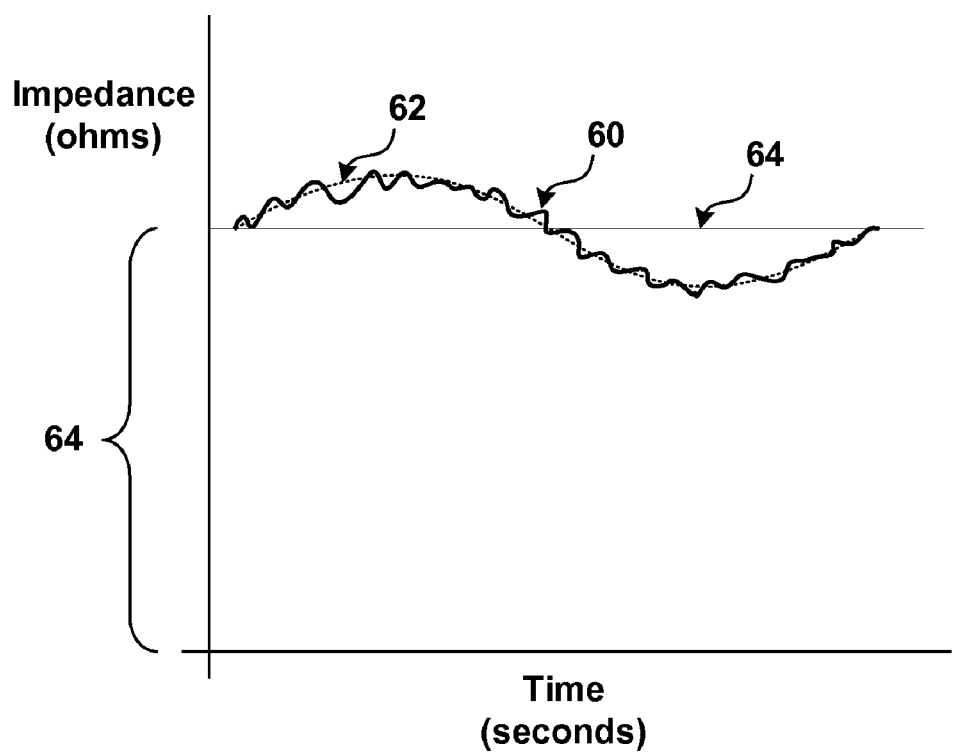
FIG. 4 is a graph of impedance measurements over time, and shows an average value, as monitored by the system of FIG. 2.

FIG. 4 is a graph of impedance measurements of a transplanted organ over time. For purposes of illustration of the invention, the measurements are shown on a substantially continuous? basis. The apparatus depicted in FIGS. 1 and 2, by contrast, may take impedance measurements on a less frequent basis, such as every minute, and ordinarily would not take impedance measurements continuously.

As shown in FIG. 4, the waveform of impedance measurements 60 is time-varying. Some of the changes in waveform 50 occur quickly, and some of the changes occur more slowly. Notably, waveform 50 includes high frequency components, which may be due to activity of the heart. Waveform 50 also includes a lower frequency component 62, depicted as a sinusoid, that may be due to a physiological effect that varies more slowly with time, such as respiration. Also present in FIG. 4 is an average value 64. Average value 64 may be referred to conventionally as the "DC component" of waveform 50, but as used herein, the term "average value" will be used.

Compared to variations in impedance caused by cardiac activity and respiration, which vary from second to second, or minute to minute, the average value 64 of impedance waveform 60 is substantially constant over short intervals of time. Over longer periods of time, however, average value 64 may or may not be constant. Changes in average value 64 over long periods of time may have clinical significance to rejection monitoring. When the organ is being rejected by the body of the patient, average value 64 slowly changes. When interstitial fluid builds up because of the onset of organ rejection, for example, average value 64 may slowly undergo a decline. The changes in average value 64 may be observable from an extended time frame, such as from day to day.

Accordingly, impedance measuring circuit 16 and processor 40 preserve average value 64. Although impedance measuring circuit 16 may employ filtering to reduce noise, impedance measuring circuit 16 ordinarily does not employ a high-pass filter to reject average value 64. Rather, impedance measuring circuit 16 or processor 40 or both identify average value 64 using any of several possible techniques. For example, impedance measuring circuit 16 or processor 40 may employ techniques to preserve average value 64 such as using analog and digital filtering, or sampling and averaging measured impedance values. Any of these techniques, or any combination of techniques, may be employed to preserve average value 64. In an embodiment in which impedance is measured every minute, for example, sampling and averaging may provide a good computation of an average value of impedance. Sampling may comprise converting an impedance measurement to a discrete value, and averaging may comprise computing the arithmetic mean of the sampled values.

Figure 5:
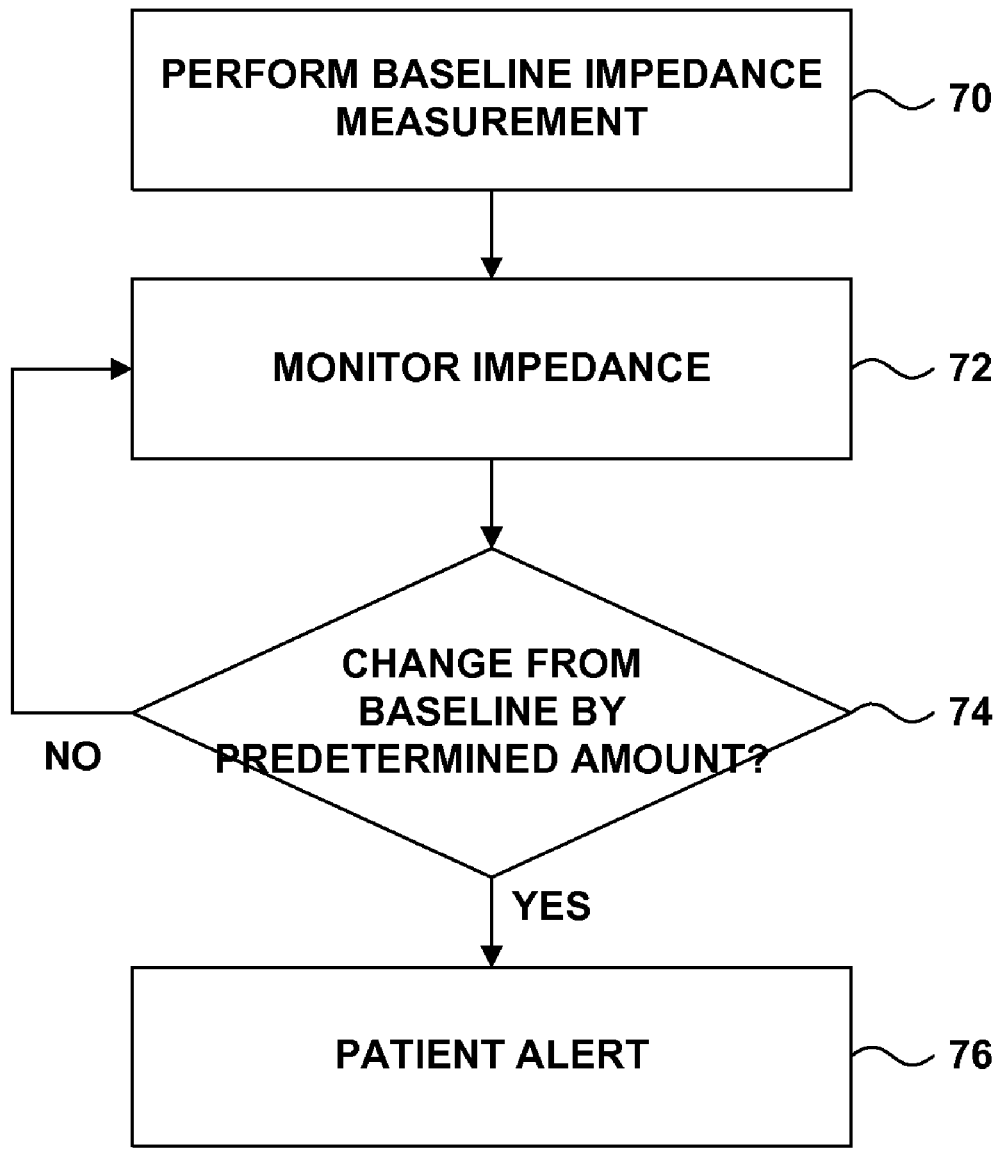
FIG. 5 is a flow diagram illustrating techniques for monitoring organ rejection with a baseline measurement.
Figure 6:
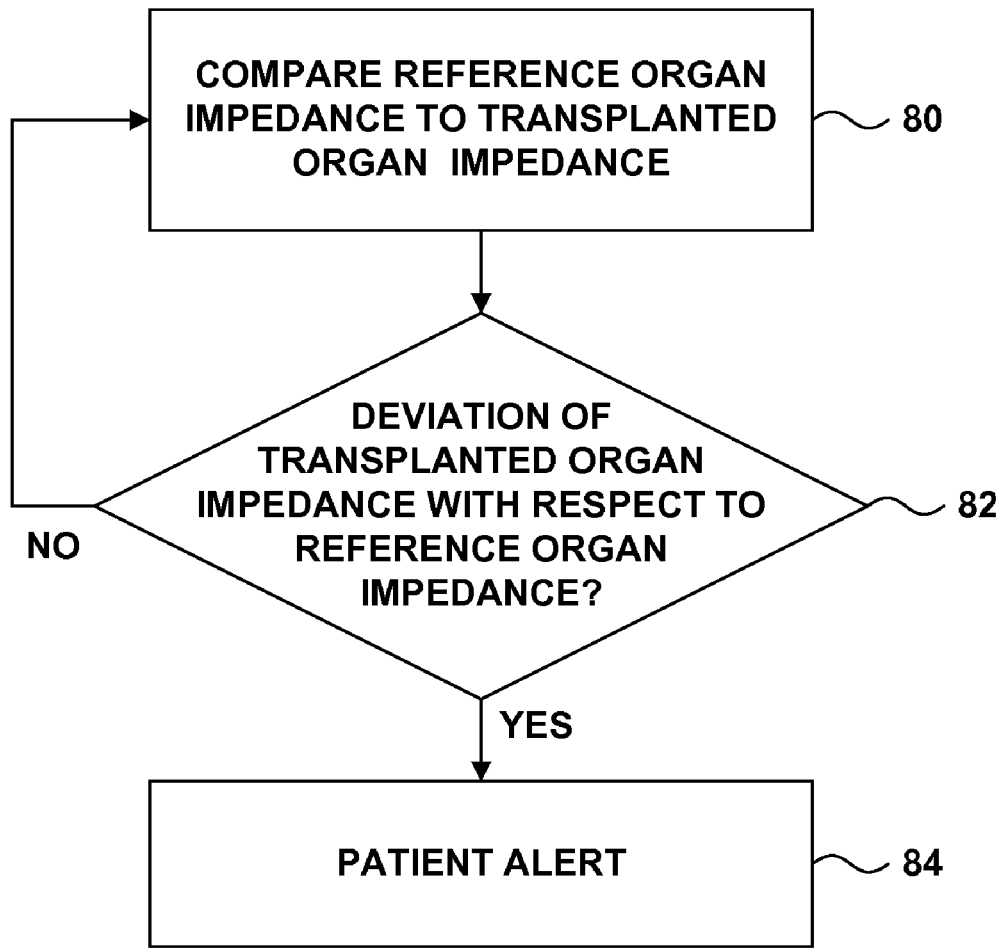
FIG. 6 is a flow diagram illustrating techniques for monitoring organ rejection with impedance measurement from a reference organ.
Figure 7:
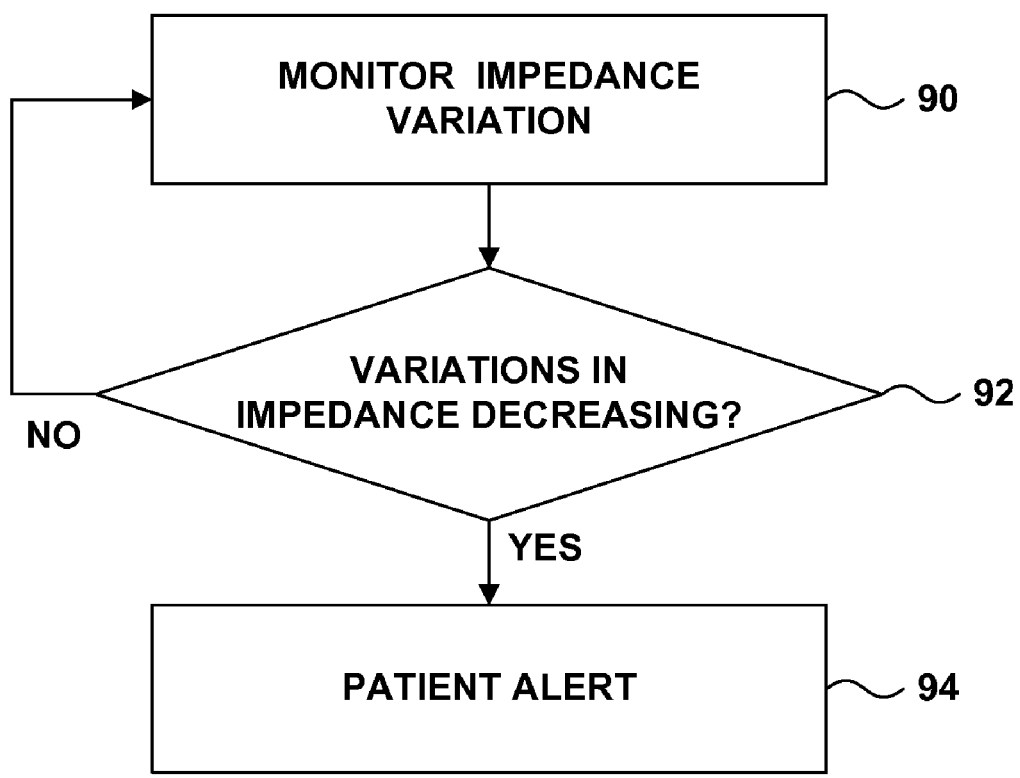
FIG. 7 is a flow diagram illustrating techniques for monitoring organ rejection by monitoring impedance variations in the transplanted organ.

FIGS. 5, 6 and 7 are flow diagrams that illustrate exemplary monitoring techniques for monitoring organ rejection. The techniques shown in FIGS. 5 and 6 use the average value of the transplanted organ impedance. The technique shown in FIG. 7 may use the average value, or may use other impedance values.

In the technique shown in FIG. 5, processor 40 obtains a baseline impedance measurement of the transplanted organ from impedance measuring circuit 16 (70). Baseline measurements may be performed some time following transplantation, such as six weeks following transplantation. It may take some time for the newly transplanted organ to become acclimated to the electrodes. During acclimation, changes in impedance measurements may reflect factors other than rejection, such as a growth of fibrous tissue around the electrodes. Although it may be difficult to use impedance measurements to monitor organ rejection during this time, the patient will often be monitored closely for several weeks after transplantation using other rejection monitoring techniques.

Once the organ becomes accustomed to the electrodes, processor 40 may obtain one or more impedance measurements to serve as a baseline (70). In particular, processor 40 may obtain a series of impedance measurements and may compute or otherwise identify an average value that serves as the baseline measurement. The baseline measurement may be stored in memory 44. A baseline measurement may be taken over a long time frame, and may comprise an average of measurements taken over several days.

Processor 40 monitors impedance measurements taken by impedance measuring circuit 16, particularly the average value of the impedance (72). Processor 40 further compares monitored impedance measurements to the baseline impedance measurement stored in memory 44. The monitored impedance may be, for example, an average value of measurements made in a single day. In other words, the monitored impedance may be a function of measurements taken over a time frame shorter than the time frame used to make the baseline impedance measurement. When there is a deviation from the baseline by a predetermined amount (74), processor 40 may generate a patient alert (76) via communication module 42. An amount of significant deviation ma be for example fifteen percent from baseline.

FIG. 6 shows another technique, in which processor 40 compares monitored impedance measurements to impedance measurements obtained from a reference organ (80). Like the impedance measurements from the transplanted organ, the impedance measurements obtained from the reference organ may be an identified average value. As noted above, monitoring system 12 may include additional electrodes, such as, e.g., electrodes 118, 120 that are used to measure the impedance at the site of reference organ, which may be a non-transplanted organ of the patient.

The reference organ need not be the same kind of organ as the transplanted organ, but may be an organ that would be expected to experience comparable changes in impedance due to physiological factors such as cardiac activity and respiration. In a case of a transplanted liver, for example, a kidney may serve as a reference organ. In general, when the transplanted organ is doing well, i.e., not experiencing significant effects of rejection, the impedance of the transplanted organ would be expected to track the impedance of the reference organ. The average impedance of the reference organ may be approximately some percentage of the impedance of the transplanted organ, or within an expected range of the impedance of the transplanted organ.

When there is a deviation of the average impedance of the transplanted organ in comparison with the average impedance of the reference organ (82), processor 40 may generate a patient alert (84) via communication module 42. A deviation may be detected when the impedance of the transplanted organ changes by a predetermined amount, such as by a predetermined standard deviation, or when the impedance of the transplanted organ no longer tracks the impedance of the reference organ. Processor 50 may, for example, normalize the measurements to put them on the same scale, and may generate a patient alert when the impedance of the transplanted organ demonstrates a fifteen percent drop with respect to the reference organ.

FIG. 7 shows an additional technique for determining whether impedance measurements indicate organ rejection. A healthy organ may typically exhibit a diurnal pattern, with impedance measurements varying over a 24-hour period. When the organ begins to experience rejection, there may be a loss of the diurnal pattern. The impedance of a rejected organ may not change when the patient goes to sleep, for example. The loss of a diurnal pattern suggests that the transplanted organ is not adapting to the daily cycles of the body of the patient.

Processor 40 may detect the loss of a diurnal pattern by monitoring impedance measurements taken by impedance measuring circuit 16 (90). In particular, processor 40 monitors a variation in impedance. Processor 40 may, for example, control impedance measuring circuit 16 to take about one impedance measurement per second, and average the measurements over a minute to obtain an impedance value for the minute. The sampling and averaging technique filters out variations in impedance that may be caused by respiration or cardiac activity. Processor 40 may monitor the impedance values from minute to minute to detect the presence or absence of a diurnal pattern. Processor 40 may also monitor the impedance values over other time intervals, such as from hour to hour.

When the organ is being rejected, the variations in measured impedance may decrease from day to day, as the diurnal pattern is lost. Processor 40 may monitor the variations in impedance (92) and may generate a patient alert (94) via communication module 42 when the variations decline by a predetermined amount.

Processor 50 may detect a decline in variation by considering the average value along with a measure of deviation of the impedance signal over a period. For example, processor 40 may compute the standard deviation of measurements made over a day. Processor 40 may evaluate variations on a daily basis or on another periodic basis.

The techniques shown in FIGS. 5, 6 and 7 are not exclusive of one another. For example, baseline impedance measurements may be used as a supplement to or in place of reference organ measurements.

The invention may offer many advantages. In embodiments described above, the monitoring system impedance monitors the impedance of the transplanted organ on a very frequent basis, such as once a minute. Although measurements taken at such intervals conserves power in the implanted power supply, the measurements are also sufficiently frequent that they are substantially continuous. In other words, the monitoring system makes impedance measurements far more frequently than the patient makes visits to the physician.

Because the monitoring is substantially continuous, the patient has an enhanced chance of early detection of organ rejection. When the monitoring system detects an organ rejection, the monitoring system alerts the patient, who may obtain early medical intervention, which in turn will reduce organ damage, reduce hospitalizations and improve patient outcomes.

Monitoring with an implanted device may also reduce the number of biopsies. Biopsies may be expensive, may cause discomfort, and may be inconvenient to the patient. In addition, a biopsy is typically a scheduled procedure, and unlike the invention, may not warn of a possible rejection in time for the patient to obtain early medical intervention.

In addition, monitoring with an implanted device provides a back-up to other therapies. Immunosuppressant drugs may be prescribed for the patient, for example, and the monitoring system may detect problems when the patient fails to comply with his medication regimen.

Furthermore, implantation of the monitoring system need not require a separate surgery. Rather, implantation of the monitoring system may be, in many cases, performed in the same operation as the transplant.

Various embodiments of the invention have been described. Although FIG. 1 depicts the monitoring system used with a kidney, the monitoring system could also be used with another transplanted organ, such as a use with liver, pancreas, lung or heart. In connection with a chambered organ such as a heart or a lung, it may be prudent to deploy additional electrodes to account for impedance changes that accompany changes in electrical activity or changes in volume. In addition, electrodes may be selectively deployed to allow for easy recovery of an average impedance value that may be compared to a baseline or to an impedance of a reference organ.

The implanted systems described herein may be, but need not be, stand-alone monitoring systems. Additional functionality may also be incorporated in the monitoring system. For example, the monitoring device may include a pacemaker or drug delivery system.

The impedance monitoring techniques described above may focus on the magnitude of the measured impedance. The invention also encompasses other attributes of impedance that may reflect organ rejection. The phase angle of the impedance, for example, which reflects the resistive and reactive components of the tissue, may also change as the character of the tissue changes during organ rejection.

The invention may be embodied in a computer-readable medium with instructions that cause a programmable processor to carry out the techniques described above. A "computer-readable medium" includes but is not limited to read-only memory, Flash memory, EPROM and a magnetic or optical storage medium. The medium may comprise instructions for causing a programmable processor to sense an impedance of a transplanted organ and determine whether the patient is experiencing rejection of the transplanted organ as a function of the impedance. The instructions may cause the processor to identify an average impedance value of the transplanted organ, for example, and compare the average impedance value to a standard, such as a baseline value from the transplanted organ or a reference value from a reference organ. These and other embodiments are within the scope of the following claims.

The invention claimed is:

1. An implantable medical device comprising:
   an impedance measuring circuit contained within the implantable medical device, wherein the impedance measuring circuit is configured to make measurements of the impedance across at least a portion of a transplanted organ in a patient;
   a processor contained within the implantable medical device, wherein the processor is configured to determine whether the patient is experiencing rejection of the transplanted organ as a function of the impedance measurements;
   a first electrode for placement in contact with the transplanted organ;
   a second electrode for placement in contact with the transplanted organ;
   a first electrode for placement in contact with a non-transplanted organ; and
   a second electrode for placement in contact with the non-transplanted organ, wherein the impedance measuring circuit is further configured to make measurements of the impedance of at least a portion of the transplanted organ with the first and second electrodes for placement in contact with the transplanted organ, and make reference measurements of the impedance of at least a portion of the non-transplanted organ with the first and second electrodes for placement in contact with the non-transplanted organ.

2. The device of claim 1, further comprising a communication module that generates a notification signal when the processor determines that the patient is experiencing rejection of the transplanted organ.

3. The device of claim 2, wherein the communication module comprises a telemetry module for communication with an external communication device.

4. The device of claim 2, wherein the communication module comprises an alert module that generates an audible alert.

5. The device of claim 1, further comprising:
a current driver that delivers an excitation current to the transplanted organ via the first and second electrodes for placement in contact with the transplanted organ.

6. The device of claim 5, wherein the impedance measuring circuit measures the impedance by comparing the voltage difference between the first and second electrodes for placement in contact with the transplanted organ with the excitation current.

7. The device of claim 5, further comprising:
a third electrode for placement in contact with the transplanted organ; and
a fourth electrode for placement in contact with the transplanted organ, wherein the impedance measuring circuit is further configured to measure the impedance by comparing the voltage difference between the third and fourth electrodes during delivery of the excitation current.

8. The device of claim 1, wherein the processor is further configured to monitor variations in the sensed impedance on a periodic basis, and determine that the patient is experiencing rejection of the transplanted organ when the variations decrease over time.

9. An implantable medical device comprising:
an impedance measuring circuit contained within the implantable medical device, wherein the impedance measuring circuit is configured to make measurements of an impedance across at least a portion of a transplanted organ in a patient, and measure an impedance across at least a portion of a reference organ in the patient; and
a processor contained within the implantable medical device, wherein the processor is configured to determine whether the patient is experiencing rejection of the transplanted organ as a function of the impedance measurements.

10. The device of claim 9, further comprising a communication module configured to generate a notification signal when the processor determines that the patient is experiencing rejection of the transplanted organ.

11. The device of claim 9, wherein the processor is further configured to determine that the patient is experiencing rejection of the transplanted organ when the impedance deviates from a reference impedance by a predetermined amount.

12. The device of claim 9, wherein the processor is further configured to obtain a plurality of impedance measurements across the portion of the transplanted organ, obtain a plurality of reference impedance measurements, identify an average value of the impedance measurements, identify a reference average value of impedance in the non-transplanted organ, and determine that the patient is experiencing rejection of the transplanted organ when the average value deviates from the reference average value by a predetermined amount.

13. The device of claim 12, wherein the processor is further configured to identify the average value of the impedance measurements by computing an arithmetic mean of the measurements.

14. The device of claim 9, further comprising:
a first electrode for placement in contact with the transplanted organ;
a second electrode for placement in contact with the transplanted organ; and
a current driver configured to deliver an excitation current to the transplanted organ via the first and second electrodes.

15. The device of claim 14, wherein the impedance measuring circuit is further configured to measure the impedance by comparing the voltage difference between the first and second electrodes with the excitation current.

16. The device of claim 14, further comprising:
a third electrode for placement in contact with the transplanted organ; and
a fourth electrode for placement in contact with the transplanted organ,
wherein the impedance measuring circuit is further configured to measure the impedance by comparing the voltage difference between the third and fourth electrodes during delivery of the excitation current.

17. The device of claim 14, further comprising:
a first electrode for placement in contact with the non-transplanted organ; and
a second electrode for placement in contact with the non-transplanted organ,
wherein the impedance measuring circuit is further configured to make measurements of the impedance of at least a portion of the transplanted organ with the first and second electrodes for placement in contact with the transplanted organ, and make reference measurements of the impedance of at least a portion of the non-transplanted organ with the first and second electrodes for placement in contact with the non-transplanted organ.

18. An implantable medical device comprising:
an impedance measuring circuit configured to make measurements of the impedance across at least a portion of a transplanted organ in a patient; and
a processor configured to monitor variations in the sensed impedance on a periodic basis, and determine that the patient is experiencing rejection of the transplanted organ when the variations decrease over time.

19. The device of claim 18, further comprising a communication module configured to generate a notification signal when the processor determines that the patient is experiencing rejection of the transplanted organ.

20. The device of claim 19, wherein the communication module comprises a telemetry module for communication with an external communication device.

21. The device of claim 19, wherein the communication module comprises an alert module configured to generate an audible alert.

22. The device of claim 18, wherein the processor is further configured to obtain a baseline impedance in the transplanted organ, and determine that the patient is experiencing rejection of the transplanted organ when the sensed impedance deviates from the baseline impedance by a predetermined amount.

23. The device of claim 18, wherein the processor is further configured to obtain a reference impedance in a non-transplanted organ, and determine that the patient is experiencing rejection of the transplanted organ when the sensed impedance deviates from the reference impedance by a predetermined amount.

24. The device of claim 18, wherein the processor is further configured to obtain a plurality of impedance measurements, and identify an average value of the impedance measurements.

25. The device of claim 24, wherein the processor is further configured to identify a baseline average value of impedance in the transplanted organ, and determine that the patient is experiencing rejection of the transplanted organ when the average value deviates from the baseline average value by a predetermined amount.

26. The device of claim 24, wherein the processor is further configured to identify a reference average value of impedance in a non-transplanted organ, and determine that the patient is experiencing rejection of the transplanted organ when the average value deviates from the reference average value by a predetermined amount.

27. The device of claim 24, wherein the processor is further configured to identify the average value of the impedance measurements by computing an arithmetic mean of the measurements.

28. The device of claim 18, further comprising:
a first electrode for placement in contact with the transplanted organ;
a second electrode for placement in contact with the transplanted organ; and
a current driver configured to deliver an excitation current to the transplanted organ via the first and second electrodes.

29. The device of claim 28, wherein the impedance measuring circuit is further configured to measure the impedance by comparing the voltage difference between the first and second electrodes with the excitation current.

30. The device of claim 28, further comprising:
a third electrode for placement in contact with the transplanted organ; and
a fourth electrode for placement in contact with the transplanted organ,
wherein the impedance measuring circuit is further configured to measure the impedance by comparing the voltage difference between the third and fourth electrodes during delivery of the excitation current.

31. The device of claim 28, further comprising:
a first electrode for placement in contact with a non-transplanted organ; and
a second electrode for placement in contact with the non-transplanted organ,
wherein the impedance measuring circuit is further configured to make measurements of the impedance of at least a portion of the transplanted organ with the first and second electrodes for placement in contact with the transplanted organ, and make reference measurements of the impedance of at least a portion of the non-transplanted organ with the first and second electrodes for placement in contact with a non-transplanted organ.

32. The device of claim 18, wherein the impedance measuring circuit and the processor are contained within the implantable medical device.

33. A method comprising:
sensing, with an implantable medical device, an impedance across at least a portion of a transplanted organ in a patient;
sensing, with the implantable medical device, a reference impedance across at least a portion of a non-transplanted organ; and
determining, with the implantable medical device, whether the patient is experiencing rejection of the transplanted organ as a function of the impedance based on the impedance and the reference impedance.

34. The method of claim 33, wherein sensing the impedance across at least a portion of a transplanted organ in a patient comprises making a plurality of impedance measurements, wherein sensing a reference impedance across at least a portion of a non-transplanted organ comprises making a plurality of reference impedance measurements, and wherein determining whether the patient is experiencing rejection of the transplanted organ comprises:
identifying an average value of the impedance measurements,
identifying a reference average value of impedance in the non-transplanted organ; and
determining that the patient is experiencing rejection of the transplanted organ when the average value deviates from the reference average value by a predetermined amount.

35. The method of claim 33, wherein determining whether the patient is experiencing rejection of the transplanted organ comprises:
determining that the patient is experiencing rejection of the transplanted organ when the impedance across the portion of the transplanted organ deviates from the reference impedance by a predetermined amount.

* * * * *